United States Patent

Barrows et al.

[11] Patent Number: 6,111,129
[45] Date of Patent: Aug. 29, 2000

[54] PROCESS FOR THE PREPARATION OF ALKANEDIOL-DIAMINOBENZOATES

[75] Inventors: Franklin H. Barrows, Waterbury; Vincent J. Gajewski, Cheshire, both of Conn.

[73] Assignee: Uniroyal Chemical Company, Inc., Middlebury, Conn.

[21] Appl. No.: 09/185,811

[22] Filed: Nov. 4, 1998

[51] Int. Cl.[7] .................................................. C07C 69/76
[52] U.S. Cl. ................................................ 560/50; 560/86
[58] Field of Search ........................................ 560/50, 86

[56] References Cited

U.S. PATENT DOCUMENTS

| | | | |
|---|---|---|---|
| 3,188,302 | 6/1965 | Lorenz | 260/77.5 |
| 3,932,360 | 1/1976 | Cerankowski et al. | 260/77.5 |
| 4,283,549 | 8/1981 | Holm | 560/50 |
| 4,476,318 | 10/1984 | Harada et al. | 560/50 |

FOREIGN PATENT DOCUMENTS

| | | | |
|---|---|---|---|
| 0 677 542 A2 | 10/1995 | European Pat. Off. | C08G 18/38 |
| 2902740 | 8/1980 | Germany. | |
| 57-120555 A2 | 7/1982 | Japan. | |
| 58-59949 A2 | 4/1983 | Japan. | |
| 61-012653 A2 | 1/1986 | Japan. | |

OTHER PUBLICATIONS

Organotin Compounds as Transesterification Catalysts. Poller et al., J. Organometallic Chemistry, 173 (3), 1979, p. C7–C8.

Database CAPLUS on STN, Acc. No. 1973:504959, Kato et al., 'Phenyl p– and m–aminobenzoates.' JP 48039458 (abstract), 1973.

*Primary Examiner*—Johann Richter
*Assistant Examiner*—Brian J. Davis
*Attorney, Agent, or Firm*—Raymond D. Thompson

[57] ABSTRACT

A process is disclosed for the direct preparation of alkanediol-diaminobenzoates comprising transesterifying an alkyl-p-aminobenzoate with a diol in the presence of a transesterification catalyst.

18 Claims, No Drawings

PROCESS FOR THE PREPARATION OF ALKANEDIOL-DIAMINOBENZOATES

BACKGROUND OF THE INVENTION

1. Field of the Invention

The present invention relates to an improved process for the preparation of alkanediol-diaminobenzoates, which are useful as curing agents for the production of polyurethane ureas.

2. Description of Related Art

Hard, impact resistant, polyurethane products are desirable in the marketplace. Good properties in the final product are dependent, inter alia, upon the use of a good curative in the manufacture of the resin.

Alkanediol-diaminobenzoates have been used as curatives for the manufacture of polyurethane ureas. These curatives have been shown to be successful replacements for the industry standard 4,4'-methylene bis(2-chloroaniline), MbOCA, which has been on the suspect carcinogens list by OSHA and other regulatory agencies.

U.S. Pat. No. 3,932,360 (Cerankowski et al.) discloses cured diamine polyurethane products prepared by combining an isocyanate terminated urethane prepolymer with a compound of the formula:

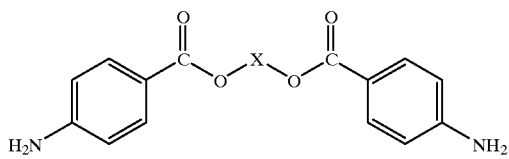

wherein X is a 2–12 carbon alkylene or cycloalkylene group, which may be substituted or unsubstituted.

These compounds were prepared by reacting p-nitrobenzoyl chloride with a diol and reducing the thus-formed compound to the diamine. This process is problematic in that it generates hydrochloric acid or amine hydrochlorides, which are corrosive and present environmental and disposal problems.

U.S. Pat. No. 4,283,549 (Holm) discloses a method of producing alkanediol-diaminobenzoates that includes esterifying nitro-benzoic acid and certain diols in a melt and then dissolving the intermediate in a solvent sparingly soluble in water, such as, an aromatic hydrocarbon, an ether, or an ester, and reducing the nitro groups with hydrogen gas. The sparingly soluble solvent is preferably anisole. The excess acid is converted to the sodium salt and removed with water. This process eliminates the corrosive aspect of hydrochloric acid. But the process, in itself, is complex and requires leaching, separation of acid, and recovery steps for the acid and the anisole solvent.

U.S. Pat. No. 4,476,318 (Harada et al.) discloses a process for the preparation of 1,3-propanediol-bis(p-aminobenzoate) wherein the process comprises reacting a p-aminobenzoic acid alkali metal salt with dihalogenated propane in an aprotic polar solvent. According to the inventors, with this process, diesterification proceeds without causing any undesirable side reactions and, therefore, the desired 1,3-propanediol bis(p-aminobenzoate) can be obtained in high purity and high yield. However, this process involves the problem of disposing of a halide-containing waste stream. It, too, requires separation and solvent recovery steps to make it efficient.

Japanes kokai 61012653 A2 discloses the manufacture of aminobenzoic acids by the reduction of nitrobenzoic acids in a water-immiscible hydrocarbon solvent in the presence of sulfur or sulfur-containing compounds and Raney nickel or sulfur-poisoned Raney nickel.

Japanese Kokai 58059949 A2 discloses the preparation of 1,3-propanediol-bis(p-aminobenzoate) by heating $Cl(CH_2)_3R$ (R=Cl, Br) with sodium or potassium p-aminobenzoate in an aprotic dipolar solvent, e.g., dimethyl formamide, dimethyl sulfoxide, or N-methylpyrrolidone. Thus, 0.15 mol of $Cl(CH_2)_3Cl$ was heated with 0.3 mol sodium p-aminobenzoate in dimethyl sulfoxide at 100° for three hours to give 91.5 percent 1,3-propanediol bis(p-aminobenzoate) of 97.4 percent purity as opposed to a 3 percent yield with ethylene glycol as solvent. $Cl(CH_2)_nCl$ (n=2, 4, 5, 8), instead of $Cl(CH_2)_3Cl$, gave the corresponding alkylene bis(p-aminobenzoates) in much lower yield.

Japanese Kokai 57120555 A2 discloses the preparation of compounds of the is structure $(H_2NC_6H_4COO)_2X$, where X=(substituted) alkylene, by esterification of the benzoic acid with a dihaloalkane in the presence of a quaternary ammonium salt.

German OLS 2902740 discloses the preparation of alkanediol-bis(aminobenzoic acid esters) by esterifying nitrobenzoates with diols $HO(CH_2)_nOH$ (n=2, 3, 5, 6) in the presence of an aromatic sulfonic acid catalyst and reducing the resulting nitro compounds.

The disclosures of the foregoing are incorporated herein by reference in their entirety.

In view e various disadvantages attendant the methods described above, it is clear that a need remains for the development of a new method for the preparation of alkanediol-di-aminobenzoates.

SUMMARY OF THE INVENTION

The present invention is directed to a process for the preparation of alkanediol-di-aminobenzoates. More particularly, the present invention is directed to a process for the direct preparation of alkanediol-bis(4-aminobenzoates) comprising, transesterifying an alkyl-p-aminobenzoate with a diol in the presence of a transesterification catalyst.

Preferably, the present invention is directed to a process whereby alkanediol-diaminobenzoates useful in the manufacture of polyurethane ureas can be prepared in one step by using an alkyl-p-aminobenzoate and transesterifying with a diol, in the presence of a transesterification catalyst, to obtain an alkanediol-bis-p-aminobenzoate directly, with the elimination of an alcohol.

DESCRIPTION OF THE PREFERRED EMBODIMENTS

According to the present invention, alkanediol-diaminobenzoates are prepared by reacting a p-aminobenzoic acid ester with a diol in the presence of a transesterification catalyst, according to the equation:

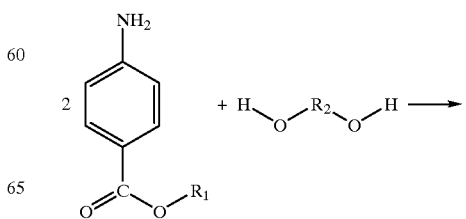

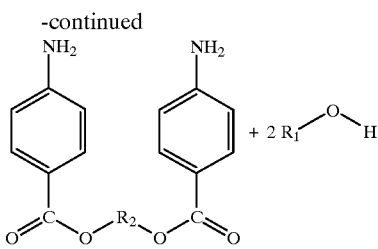

where R₁ is an alkyl moiety of from 1 to 12 carbon atoms, which may be straight-chain or branched, e.g., methyl, ethyl, propyl, butyl, hexyl, heptyl, octyl, nonyl, decyl, undecyl, dodecyl, and isomers thereof. It is preferred that R₁ have from one to eight carbon atoms and more preferred that it have from one to four carbon atoms, i.e., methyl, ethyl, propyl, butyl, and isomers thereof. The most preferred alkyl-p-aminobenzoate for use in the practice of this invention is ethyl 4-aminobenzoate.

R₂ is a 1–12 carbon alkylene or cycloalkylene moiety, which may be substituted or unsubstituted. Suitable substituents include C₁ to C₅ alkyl groups; halogen, e.g., bromo, chloro, fluoro; and aryl groups, preferably phenyl. In a particularly preferred embodiment, R₂ is an alkylene moiety having an odd number of carbon atoms, more preferably, three or five carbon atoms, i.e., propylene or pentylene.

The following diols are exemplary of those that can be used in the reaction of is the present invention:
- 1,3-butanediol,
- 1,4-butanediol,
- 2,3-butanediol,
- 2-n-butyl-2-ethyl- 1,3-propanediol,
- 3-chloro- 1,2-propanediol,
- 1,4-cyclohexanediol,
- 2,5-dimethyl-2,5-hexanediol,
- 2,2-dimethlyl-1,3-propanediol,
- 2,2-diphenyl-1,3-propanediol,
- 1, 12-dodecanediol,
- ethylene glycol,
- 2-ethyl- 1,3-hexanediol,
- 2-ethyl-2-methyl- 1,3-propanediol,
- 1,7-heptanediol,
- 1,6-hexanediol,
- 2,5-hexanediol,
- 2-methyl- 1,4-butanediol,
- 2-methyl-2,4-pentanediol,
- 2-methyl-1,3-propanediol,
- 1,8-octanediol,
- 1,5-pentanediol,
- 2,4-pentanediol,
- 1-phenyl-1,2-ethanediol,
- 1,2-propanediol,
- 1,3-propanediol,
- 1,1,4,4-tetraphenyl-1,4-butanediol, and
- 2,2,4,4-tetramethyl- 1,3-cyclobutanediol.

A preferred diol is 1,3-propanediol.

Any transesterification catalyst can be used, but tin compounds, especially dibutyltindiacetate, are preferred. An exemplary listing of catalysts that can be employed in the practice of the present invention includes stannous octoate, stannous oxalate, dibutyltindilaurate, dioctyltindilaurate, dibutyltindi-2-ethylhexoate, tetraisopropyl titanate, tetrabutyl titanate, tetrakis-2-ethylhexyl titanate, dibutyltindilaury mercaptide, dibutyltindiisooctylmercapto acetate, dioctyltindilauryl mercaptide, dimethyltindilauryl mercaptide, dimethyltindiisooctylmercapto acetate, dibutyltin oxide, butyl stannoic acid, and the like.

The alkylaminobenzoate to diol ratio can be stoichiometric, i.e., 2:1, but the use of an excess of alkylaminobenzoate, e.g., in the range of greater than 2:1 up to about 5:1, preferably from greater than 2:1 up to about 3:1, is permissible and, in certain cases, may be found to be advantageous.

The reaction can be carried out in a temperature range of about 100° C. to about 180° C., but a range of about 110° C. to about 160° C. is preferred, and a range of about 120° C. to about 140° C. is more preferred.

Once obtained, the product can be easily purified via crystallization from alcohol, preferably an alcohol having from one to eight, more preferably, from one to four carbon atoms, e.g. methanol, ethanol, propanol, butanol, pentanol, hexanol, heptanol, octanol, and the like, and isomers thereof.

The crystallization solvent can be readily recycled. The filtrate bottoms that contain any excess alkylaminobenzoate, monoester and/or catalyst can be recycled to the next batch without detriment, making the process of the present invention one that is economically efficient and environmentally beneficial.

The alkanediol-diaminobenzoate curing agents prepared by the process of the present invention are capable of curing isocyanate terminated urethane prepolymers to provide strong, rubbery, abrasion-resistant solids in conventional hot molding or in solvent based coating systems.

For solvent-based systems the curing agents are soluble in several conventional solvents used for coating techniques and possess kinetics that provide useful working times and conditions and also provide the desired three-dimensional structure in the cured polyurethanes.

In conventional hot molding techniques the curing agents prepared by the process of the present invention possess melting points generally within the desired range for such techniques and a reasonable degree of supercooling properties, are compatible with a wide range of isocyanate terminated urethane prepolymers, and, in general, exhibit kinetics that provide useful pot lives and curing times. In addition, the curing agents are generally stable to decomposition at their melting points.

Suitable isocyanate terminated urethane prepolymers for use with the curing agents prepared by the process of the present invention are known in the art and are disclosed, for example, in , *Advances in Urethane Science and Technology*, Vol. 1, K. D. Frisch and S. L. Regan (Technomic Publishing Company, New Jersey, 1971) and *Polyurethane Coatings*, Keith Johnson (Noyes Data Corporation, New Jersey, 1972). Such isocyanate terminated prepolymers include those generally designated in the art as "polyester" and "polyether" types. Examples of preferred isocyanate terminated urethane prepolymers are disclosed in U.S. Pat. No. 3,188,302, incorporated herein by reference.

The curing agents prepared by the process of the present invention can be employed singly or in a combination of two or more in order to obtain the optimum properties of each curing agent. It should also be understood that conventional additives can be employed in the prepolymer/curing agent composition, such as, catalysts, fillers, plasticizers, and the like.

Polyurethane products cured using the curing agents prepared by the process of the present invention can be employed wherever conventional polyurethanes are employed. For example, they are particularly useful for machine parts, potting and encapsulation of electronic equipment, and as a metal replacement. The specific properties of such products will depend upon the specific isocyanate terminated prepolymer, the specific diamine curing agent, the ratio of isocyanate to amine, and the curing cycle employed.

The curing agents prepared by the process of the present invention are satisfactorily employed in curing isocyanate terminated urethane prepolymers when used at a ratio of about 0.5:1 to about 2:1 based on moles of amine to moles of isocyanate and, more preferably, at a ratio of about 0.8:1 to about 1.2: 1.

Examples V and VI of U.S. Pat. No. 3,932,360 provide useful descriptions, respectively, of the diamine curing of an isocyanate terminated urethane prepolymer by the hot melt technique and by the solvent method.

According to the first of those disclosures, 10 grams of a commercially available isocyanate terminated prepolymer containing 4 percent by weight of available NCO groups and prepared from polytetrametilylene ether glycol and 2,4-toluene diisocyanate (ADIPRENE L-100, E. I. duPont de Nemours & Co.) is heated in a glass vessel to 110° C. Then, 1.4 grams of 1,3-propanediol di-p-aminobenzoate is melted and heated to 150° C. The diamine is then added to the prepolymer, with thorough stirring. The mixture is then degassed and poured into a metal mold preheated to 110° C. The mold and its contents are maintained at 110° C. for three hours, whereby a tough, cured polyurethane elastomer is obtained upon removal therefrom.

According to the second of the disclosures, 1.3 grams of 1,3-propanediol di-p-aminobenzoate is dissolved in 10 grams of 2-ethoxyethyl acetate with slight warming, and the thus formed solution is added to 10 grams of ADIPRENE L-100 and stirred thoroughly. The viscosity stability of the resulting solution is suitable for most applications. The solution is applied to glass and metal surfaces by spraying, dipping, and draw-down techniques and cured at 110° C. for three hours, whereby tough elastomeric films are obtained.

Various features and aspects of the present invention are illustrated further in the examples that follow. While these examples are presented to show one skilled in the art how to operate within the scope of the invention, they are not intended in any way to serve as a limitation upon the scope of the invention.

EXAMPLE 1

A mixture of 123.9 grams (0.75 mole) of ethyl 4-amino-benzoate, 22.83 grams (0.3 mole) of 1,3-propanediol, and 3.42 grams of dibutyltindiacetate was placed in a 500-milliliter, four-necked, round-bottom flask equipped with a thermocouple, a mechanical stirrer, a distillation head, and a subsurface nitrogen is sweep. Over a period of one-half hour, the reaction mixture was heated to 130° C. and held for an additional nine hours at 130° C. as the ethanol produced by the reaction distilled off. The progress of the reaction was followed using high performance liquid chromatography by observing the disappearance of the starting ethyl 4-amino-benzoate and the conversion of the intermediate monoester to the 20 diester. The reaction mixture was added to 848 grams of isopropanol. On cooling, 1,3-propanediol-bis(4-aminobenzoate) precipitated and was isolated by filtration. The filter cake was washed with 84.8 grams of isopropanol and dried to a constant weight of 77.4 grams (82.2 percent yield). The melting point was 121° to 126° C., and relative area HPLC analysis of the product showed it to be 93.4 percent pure. The infrared spectrum was consistent with the structure.

EXAMPLE 2

The filtrate and washings from Example 1 were vacuum-stripped to remove the isopropanol. The residue, 44.1 grams, 101.6 grams (0.615 mole) of ethyl 4-amino-benzoate, 22.83 grams (0.3 mole) of 1,3-propanediol, and 0.23 gram of dubutyltindiacetate, were placed in the apparatus described in Example 1. The reaction procedure of Example 1 was repeated and produced 95.7 grams (101.6 percent yield) of material. Relative area HPLC analysis showed it to be 95.5 percent pure.

EXAMPLE 3

The procedure used in Example 2 produced 43.7 grams of residue that, along with 99.1 grams (0.6 mole) of ethyl 4-amino-benzoate, 22.83 grams (0.3 mole) of 1,3-propanediol, and 0.69 gram of dibutyltindiacetate, was placed in the reaction is apparatus described in Example 1. Following the same procedure as in Example 1, 95.5 grams (101.4 percent yield) of 1,3-propanediol bis(4-aminobenzoate) was isolated. Relative area HPLC analysis showed it to be 95.6 percent pure. The average yield for the three reactions was 95.1 percent with an average purity of 94.8 relative area percent.

EXAMPLE 4

This example illustrates that isopropanol is not the only alcohol that can be used to isolate 1,3-propanediol-bis(4-aminobenzoate). Using the procedure described in Examples 1 through 3 for preparation, 1,3-propanediol-bis(4-aminobenzoate) was isolated by crystallization from 376 grams of ethanol. The filter cake was washed with 38 grams of ethanol. The results are shown in TABLE 1.

TABLE 1

| A | B | C | D | E | F | G | H |
|---|---|---|---|---|---|---|---|
| 1 | 123.9 | 22.83 | 3.42 | — | 73.6 | 78.1 | 96.6 |
| 2 | 99.1 | 22.83 | 0.23 | 46.9 | 93.0 | 98.7 | 96.1 |
| 3 | 101.6 | 22.83 | 0.69 | 48.8 | 93.8 | 99.6 | 93.0 |

A—Run Number
B—Grams of ethyl-4-aminobenzoate.
C—Grams of 1,3-propanediol.
D—Grams of catalyst.
E—Grams of residue.
F—Yield in grams.
G—Yield in percent.
H—Relative area percent assay.

The average yield was 92.1 percent with an average purity of 95.2 relative area percent.

EXAMPLE 5

Polyurethane Urea from 1,3-Propanediol-bis(4-aminobenzoate)

Seventeen grams of 1,3-propanediolbis(4-aminobenzoate) prepared as in Example 1 was heated to melt and stirred thoroughly into 100 grams of Vibrathane B635 (Uniroyal Chemical Company), a TDI/polytetramethylene ether glycol prepolymer with a 4.2 percent residual NCO, at 100° C. The mixture was degassed for approximately one minute and then cast into a metal mold at 115° C. The sheets were post cured for 16 hours at 115° C.

EXAMPLE 6

Polyurethane Urea from 1,3-Propanediolbis(4-aminobenzoate)

12.8 grams of the 1,3-propanediolbis(4-aminobenzoate) of Example 3 was heated to melt and stirred thoroughly into 100 grams of Adiprene PP1095 (Uniroyal Chemical Company), a paraphenylene diisocyanate/polyester prepolymer with a 3,4 percent residual NCO, at 80° C. The mixture was degassed until the foam head broke and then cast into a metal mold at 115° C. The sheets were post cured for 16 hours at 115° C.

The physical properties of the products of Example 5 and 6 are reported in TABLE 2.

TABLE 2

| PHYSICAL PROPERTIES | EXAMPLE 5 | EXAMPLE 6 |
| --- | --- | --- |
| DUROMETER SHORE A | 90–92 | 92–94 |
| 100% MODULUS psi | 1200 | 1150 |
| 300% MODULUS psi | 1800 | 1700 |
| TENSILE STRENGTH psi | 4200 | 5000 |
| ELONGATION % | 430 | 600 |
| TEAR STRENGTH pli | 500 | 600 |

In view of the many changes and modifications that can be made without departing from principles underlying the invention, reference should be made to the appended claims for an understanding of the scope of the protection to be afforded the invention.

What is claimed is:

1. A process for the direct preparation of alkanediol-diaminobenzoates comprising reacting an alkyl-p-aminobenzoate with a diol, in a ratio of at least two moles of alkyl-p-aminobenzoate per mole of diol, in the presence of a transesterification catalyst selected from the group consisting of stannous octoate, stannous oxalate, dibutyltindilaurate, dioctyltindilaurate, dibutyltindi-2-ethylhexoate, tetraisopropyl titanate, tetrabutyl titanate, tetrakis-2-ethylhexyl titanate, dibutyltindilauryl mercaptide, dibutyltindiisooctylmercapto acetate, dioctyltindilauryl mercaptide, dimethyltindilauryl mercaptide, dimethyltindi-isooctylmercapto acetate, dibutyltindiacetate, dibutyltin oxide, and butyl stannoic acid, according to the equation:

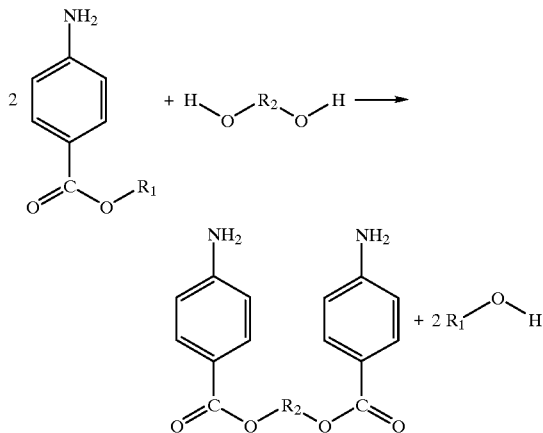

where $R_1$ is a straight-chain or branched alkyl moiety and $R_2$ is a substituted or unsubstituted alkylene or cycloalkylene moiety.

2. A process for the preparation of alkanediol-diaminobenzoates comprising reacting at least two moles of a p-aminobenzoic acid ester per mole of a diol in the presence of dibutyltindiacetate, according to the equation:

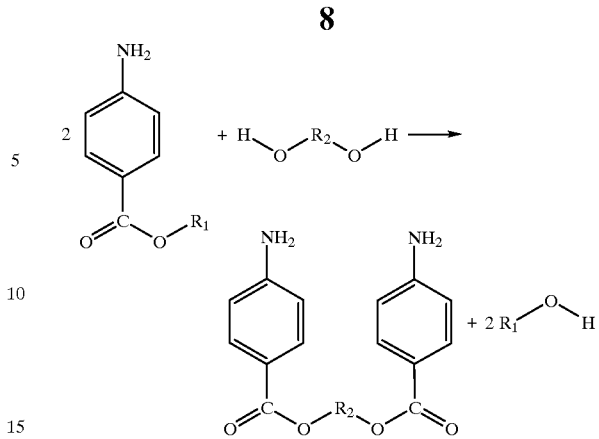

where $R_1$ is a straight-chain or branched alkyl moiety and $R_2$ is a substituted or unsubstituted alkylene or cycloalkylene moiety.

3. The process of claim 2 wherein $R_1$ is a straight-chain or branched alkyl moiety of 1 to 12 carbon atoms.

4. The process of claim 2 wherein $R_1$ is ethyl.

5. The process of claim 2 wherein $R_2$ is a substituted or unsubstituted alkylene or cycloalkylene moiety of 1 to 12 carbon atoms.

6. The process of claim 5 wherein $R_2$ is a substituted alkylene moiety wherein a substituent is selected from the group consisting of alkyl groups of one to five carbon atoms, halogens, and aryl groups.

7. The process of claim 2 wherein the diol is selected from the group consisting of:
   1,3-butanediol,
   1,4-butanediol,
   2,3-butanediol,
   2-n-butyl-2-ethyl-1,3-propanediol,
   3-chloro-1,2-propanediol,
   1,4-cyclohexanediol,
   2,5-dimethyl-2,5-hexanediol,
   2,2-dimethyl-1,3-propanediol,
   2,2-diphenyl-1,3-propanediol,
   1,12-dodecanediol,
   ethylene glycol,
   2-ethyl-1,3-hexanediol,
   2-ethyl-2-methyl-1,3-propanediol,
   1,7-heptanediol,
   1,6-hexanediol,
   2,5-hexanediol,
   2-methyl-1,4-butanediol,
   2-methyl-2,4-pentanediol,
   2-methyl-1,3-propanediol,
   1,8-octanediol,
   1,5-pentanediol,
   2,4-pentanediol,
   1-phenyl-1,2-ethanediol,
   1,2-propanediol,
   1,3-propanediol,
   1,1,4,4-tetraphenyl-1,4-butanediol, and
   2,2,4,4-tetramethyl-1,3-cyclobutanediol.

8. The process of claim 7 wherein the diol is 1,3-propanediol.

9. The process of claim 2 wherein the reaction is carried out at a temperature in the range of about 100° C. to about 180° C.

10. The process of claim 2 further comprising the step of purifying the alkanediol-diaminobenzoate by crystallization from alcohol.

11. The process of claim 10 wherein the alcohol is one having from one to eight carbon atoms.

12. The process of claim 9 further comprising the step of purifying the alkanediol-diaminobenzoate by crystallization from alcohol.

13. The process of claim 12 wherein the alcohol is one having from one to eight carbon atoms.

14. A process for the preparation of 1,3-propanediol bis(4-aminobenzoate) comprising reacting at least two moles of ethyl 4-aminobenzoate per mole of 1,3-propanediol in the presence of dibutyltindiacetate at a temperature in the range of about 100° C. to about 180° C. according to the equation:

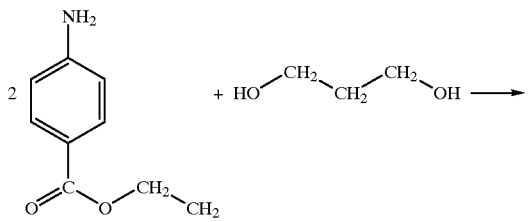
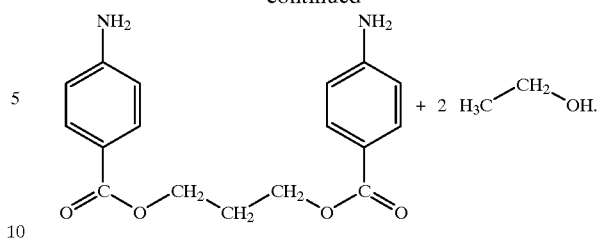

15. The process of claim 14 further comprising the step of purifying the 1,3-propanediol-bis(4-aminobenzoate) by crystallization from alcohol.

16. The process of claim 15 wherein the alcohol is one having from one to eight carbon atoms.

17. The process of claim 16 wherein the alcohol is one having from one to four carbon atoms.

18. The process of claim 17 wherein the alcohol is ethanol or isopropanol.

* * * * *